United States Patent
Irisawa (10) Patent No.: US 11,369,342 B2
(45) Date of Patent: Jun. 28, 2022

(54) PHOTOACOUSTIC IMAGE GENERATION APPARATUS AND INSERT

(71) Applicant: FUJIFILM SonoSite, Inc., Bothell, WA (US)

(72) Inventor: Kaku Irisawa, Kanagawa (JP)

(73) Assignee: FUJIFILM SonoSite, Inc., Bothell, WA (US)

( * ) Notice: Subject to any disclaimer, the term of this patent is extended or adjusted under 35 U.S.C. 154(b) by 1105 days.

(21) Appl. No.: 15/824,719

(22) Filed: Nov. 28, 2017

(65) Prior Publication Data

US 2018/0078235 A1    Mar. 22, 2018

Related U.S. Application Data (63) Continuation of application No. PCT/JP2016/003036, filed on Jun. 23, 2016.

(30) Foreign Application Priority Data

Jun. 30, 2015    (JP) .............................. JP2015-131069

(51) Int. Cl.
*A61B 5/00* (2006.01)
*A61B 8/13* (2006.01)
(Continued)

(52) U.S. Cl.
CPC .............. *A61B 8/13* (2013.01); *A61B 5/0035* (2013.01); *A61B 5/0095* (2013.01);
(Continued)

(58) Field of Classification Search
CPC ......... A61B 8/13; A61B 5/0095; A61B 10/04; A61B 10/02; A61B 2010/045
See application file for complete search history.

(56) References Cited

U.S. PATENT DOCUMENTS

| 2006/0069313 A1* | 3/2006 | Couvillon .............. A61B 5/064 600/179 |
| 2013/0237802 A1* | 9/2013 | Irisawa ................ A61B 5/0095 600/407 |

(Continued)

FOREIGN PATENT DOCUMENTS

| JP | 2013-13713 A |   | 1/2013 |              |
| JP | 2013013713   | * | 1/2013 | .............. A61B 5/06 |
| JP | 2015-37519 A |   | 2/2015 |              |
| JP | 2015-43969 A |   | 3/2015 |              |

OTHER PUBLICATIONS

International Preliminary Report on Patentability and Written Opinion of the International Searching Authority (Forms PCT/IB/326, PCT/IB/373 and PCT/ISA/237) for International Application No. PCT/JP2016/003036, dated Jan. 11, 2018, including an English translation of the Written Opinion.

(Continued)

*Primary Examiner* — Rochelle D Turchen
(74) *Attorney, Agent, or Firm* — Heslin Rothenberg Farley & Mesiti P.C.

(57) ABSTRACT

Provided are a photoacoustic image generation apparatus and an insert that can evaluate whether a plurality of materials with different absorption wavelengths are present in the vicinity of a puncture needle, without preparing a plurality of light sources. A puncture needle is at least partially inserted into a subject. An optical fiber guides light with a first wavelength. A light emitting portion emits the light guided by the optical fiber. A light absorption/conversion member absorbs the light with the first wavelength emitted from the light emitting portion and converts the light with the first wavelength into light with a second wavelength. In addition, the light absorption/conversion member generates photoacoustic waves with the conversion into the light with the second wavelength.

16 Claims, 6 Drawing Sheets

(51) Int. Cl.
- *A61B 8/00* (2006.01)
- *A61B 8/08* (2006.01)
- *A61B 8/12* (2006.01)
- *A61B 10/02* (2006.01)
- *A61B 10/04* (2006.01)

(52) U.S. Cl.
CPC .............. *A61B 5/6849* (2013.01); *A61B 8/12* (2013.01); *A61B 8/4416* (2013.01); *A61B 8/5207* (2013.01); *A61B 8/5246* (2013.01); *A61B 10/02* (2013.01); *A61B 10/04* (2013.01); *A61B 2010/045* (2013.01); *A61B 2505/05* (2013.01); *A61B 2560/063* (2013.01); *A61B 2576/00* (2013.01)

(56) References Cited

U.S. PATENT DOCUMENTS

| | | | |
|---|---|---|---|
| 2014/0288351 A1* | 9/2014 | Jones | A61N 5/0624 600/9 |
| 2015/0297092 A1 | 10/2015 | Irisawa | |
| 2016/0135689 A1 | 5/2016 | Murakoshi | |

OTHER PUBLICATIONS

International Search Report (Form PCT/ISA/210) for International Application No. PCT/JP2016/003036, dated Oct. 18, 2016, including an English translation.

\* cited by examiner

PHOTOACOUSTIC IMAGE GENERATION APPARATUS AND INSERT

CROSS-REFERENCE TO RELATED APPLICATION

The present application is a Continuation of PCT International Application No. PCT/JP2016/003036 filed on Jun. 23, 2016, which claims priority under 35 U.S.C. § 119(a) to Japanese Patent Application No. 2015-131069 filed on Jun. 30, 2015. Each of the above applications is hereby expressly incorporated by reference, in its entirety, into the present application.

BACKGROUND

Technical Field

The present invention relates to a photoacoustic image generation apparatus, and more particularly, to a photoacoustic image generation apparatus that detects photoacoustic waves generated by the absorption of light by a light absorber and generates a photoacoustic image.

In addition, the invention relates to an insert such as a puncture needle used in the photoacoustic image generation apparatus.

2. Description of the Related Art

An ultrasonography method has been known as a kind of image inspection method that can non-invasively inspect the internal state of a living body. In ultrasonography, an ultrasound probe that can transmit and receive ultrasonic waves is used. In a case in which the ultrasound probe transmits ultrasonic waves to a subject (living body), the ultrasonic waves travel in the living body and are reflected from the interface between tissues. The ultrasound probe receives the reflected ultrasonic waves and a distance is calculated on the basis of the time until the reflected ultrasonic waves return to the ultrasound probe. In this way, it is possible to capture an image indicating the internal aspect of the living body.

In addition, photoacoustic imaging has been known which captures the image of the inside of a living body using a photoacoustic effect. In general, in the photoacoustic imaging, the inside of the living body is irradiated with pulsed laser light such as a laser pulse. In the inside of the living body, a living body tissue absorbs the energy of the pulsed laser light and ultrasonic waves (photoacoustic waves) are generated by adiabatic expansion caused by the energy. For example, an ultrasound probe detects the photoacoustic waves and a photoacoustic image is formed on the basis of a detection signal. In this way, it is possible to visualize the inside of the living body on the basis of the photoacoustic waves.

For the photoacoustic imaging, JP2015-37519A discloses a technique in which light emitted from a light source is guided to the vicinity of a leading end of a puncture needle by, for example, an optical fiber and is emitted from the leading end to a photoacoustic wave generation portion of the puncture needle. The photoacoustic wave generation portion includes, for example, a light absorption member. JP2015-37519A discloses a technique in which the light absorption member can be made of, for example, an epoxy resin, a polyurethane resin, or a fluorine resin with which a black pigment is mixed, silicon rubber, or a black paint having high light absorbance with respect to the wavelength of laser light. In addition, JP2015-37519A discloses a technique in which a metal film or an oxide film having light absorptivity with respect to the wavelength of laser light is used as the light absorption member. An ultrasound probe detects the photoacoustic waves generated by the emission of light to the photoacoustic wave generation portion and a photoacoustic image is generated on the basis of a detection signal of the photoacoustic waves. In the photoacoustic image, a part of the photoacoustic wave generation portion appears as a bright point, which makes it possible to check the position of the puncture needle using the photoacoustic image.

Furthermore, JP2013-13713A discloses a puncture needle including a light emitting portion. In JP2013-13713A, light emitted from a light source is guided to the light emitting portion of the puncture needle by, for example, an optical fiber and is emitted from the light emitting portion to the outside. In a subject, photoacoustic waves are generated due to the absorption of the light emitted from the light emitting portion. An ultrasound probe detects the photoacoustic waves generated by the absorption of the light emitted from the light emitting portion of the puncture needle and a photoacoustic image is generated on the basis of the detection signal of the photoacoustic waves. In this way, it is possible to check the position of the puncture needle.

SUMMARY

Here, for example, in a case in which the puncture needle is inserted into a blood vessel, an operator can determine whether the leading end of the puncture needle has been inserted into the blood vessel, on the basis of whether blood has flowed into the needle or a base portion of the needle. However, in JP2015-37519A and JP2013-13713A, since the light guide member, such as an optical fiber, passes through the needle, the inflow path of blood is narrower than that in a case in which, for example, the optical fiber is not provided. Therefore, it takes time for the inflow of blood and it takes time to determine whether the leading end of the puncture needle has been inserted into the blood vessel.

In JP2015-37519A, the light absorber provided at the leading end of the needle generates photoacoustic waves and the light absorber absorbs almost all of the light emitted to the photoacoustic wave generation portion. Therefore, even in a situation in which the light absorber is present in front of the needle in a needling direction in the subject, it is difficult for the light absorber to generate photoacoustic waves. For this reason, in JP2015-37519A, only the positional information of the leading end of the needle can be acquired and it is difficult to acquire surrounding environment information such as information indicating whether the light absorber is present in the vicinity of the needle. In contrast, in JP2013-13713A, the light absorber that is present in front of the needle in the needling direction in the subject is irradiated with the light emitted from the light emitting portion. Therefore, in a case in which light with a wavelength absorbed by blood (blood vessel) is emitted from the light emitting portion, it is possible to determine whether the leading end of the needle has been inserted into the blood vessel on the basis of whether a bright point is present in the photoacoustic image.

However, in JP2013-13713A, it is necessary to prepare light sources corresponding to the number of absorption wavelengths in order to evaluate whether a plurality of materials with different absorption wavelengths are present in the vicinity of the puncture needle. JP2013-13713A has the problem that the overall cost of the apparatus increases with an increase in the number of light sources. This problem is not limited to the puncture needle and may also occur in a case in which the positional information and surrounding environment information of other inserts to be inserted into the subject, such as catheters or guide wires, are acquired by a photoacoustic image.

The invention has been made in view of the above-mentioned problems and an object of the invention is to provide a photoacoustic image generation apparatus that can evaluate whether a plurality of materials with different absorption wavelengths are present in the vicinity of a puncture needle, without preparing a plurality of light sources.

In addition, an object of the invention is to provide an insert that is used in the photoacoustic image generation apparatus.

In order to achieve the objects, the invention provides an insert that is at least partially inserted into a subject. The insert includes: a light guide member that guides light with a first wavelength; a light emitting portion from which the light guided by the light guide member is emitted; and a light absorption/conversion member that absorbs the light with the first wavelength emitted from the light emitting portion, converts the light with the first wavelength into light with a second wavelength different from the first wavelength, and generates photoacoustic waves with the conversion into the light with the second wavelength.

In the insert according to the invention, preferably, the light absorption/conversion member covers at least a part of a light emission surface of the light emitting portion.

The light absorption/conversion member may include a phosphor that absorbs the light with the first wavelength and converts the light with the first wavelength into the light with the second wavelength and a resin including the phosphor.

The insert according to the invention may have an inner cavity. The light absorption/conversion member may function as a fixing member that fixes the light guide member to an inner wall of the inner cavity.

The insert according to the invention may further include a transparent resin that transmits the light with the second wavelength. The light absorption/conversion member may be covered with the transparent resin. In a case in which the insert has an inner cavity, the light guide member and the light absorption/conversion member may be fixed to an inner wall of the inner cavity of an insert by the transparent resin.

The insert according to the invention may be a puncture needle having an inner cavity. In this case, the insert may further include a hollow tube in which the light guide member is accommodated.

The puncture needle may include an inner needle and an outer needle. The inner needle may include the hollow tube. The inner needle may seal at least a portion of the inner cavity of the outer needle.

The light absorption/conversion member may function as a fixing member that fixes the light guide member to an inner wall of the hollow tube.

The insert according to the invention may further include a transparent resin that transmits the light with the second wavelength. The light guide member and the light absorption/conversion member may be fixed to an inner wall of the hollow tube by the transparent resin.

In addition, the invention provides a photoacoustic image generation apparatus including: a light source that emits light with a first wavelength; an insert that is at least partially inserted into a subject and includes a light guide member that guides the light with the first wavelength, a light emitting portion from which the light guided by the light guide member is emitted, and a light absorption/conversion member that absorbs the light with the first wavelength emitted from the light emitting portion, converts the light with the first wavelength into light with a second wavelength different from the first wavelength, and generates first photoacoustic waves with the conversion into the light with the second wavelength; acoustic wave detection means for detecting the first photoacoustic waves and second photoacoustic waves which are generated in the subject by the emission of the light with the second wavelength to the subject; and photoacoustic image generation means for generating a photoacoustic image on the basis of the first photoacoustic waves and the second photoacoustic waves.

Preferably, the photoacoustic image generation apparatus according to the invention further includes peak detection means for detecting one or more peaks having a larger signal value than the surroundings in the photoacoustic image.

Preferably, the photoacoustic image generation apparatus according to the invention further includes: peak tracking means for temporally tracking the signal value of the detected peak; determination means for determining whether the insert is close to a material that generates the second photoacoustic waves, on the basis of a change in the tracked signal value; and notification means for notifying a determination result of the determination means.

In a case in which the peak tracking means detects two peaks, the determination means may determine that the insert is close to the material that generates the second photoacoustic waves.

In a case in which the change in the signal value is equal to or greater than a threshold value, the determination means may determine that the insert is close to the material that generates the second photoacoustic waves.

Preferably, the second wavelength is a wavelength indicating absorptivity in light absorbance-wavelength characteristics of a material that is present at an insertion target position of the insert.

The acoustic wave detection means may further detect reflected acoustic waves with respect to acoustic waves transmitted to the subject. In this case, preferably, the photoacoustic image generation apparatus according to the invention further includes reflected acoustic image generation means for generating a reflected acoustic image on the basis of the reflected acoustic waves.

The photoacoustic image generation apparatus according to the invention may further include image combination means for combining the photoacoustic image and the reflected acoustic image.

The photoacoustic image generation apparatus and the insert according to the invention can evaluate whether a plurality of materials with different absorption wavelengths are present in the vicinity of a puncture needle, without preparing a plurality of light sources.

BRIEF DESCRIPTION OF THE DRAWINGS

Exemplary embodiments of the present invention will be described in detail based on the following figures, wherein.

DETAILED DESCRIPTION

Figure 1:
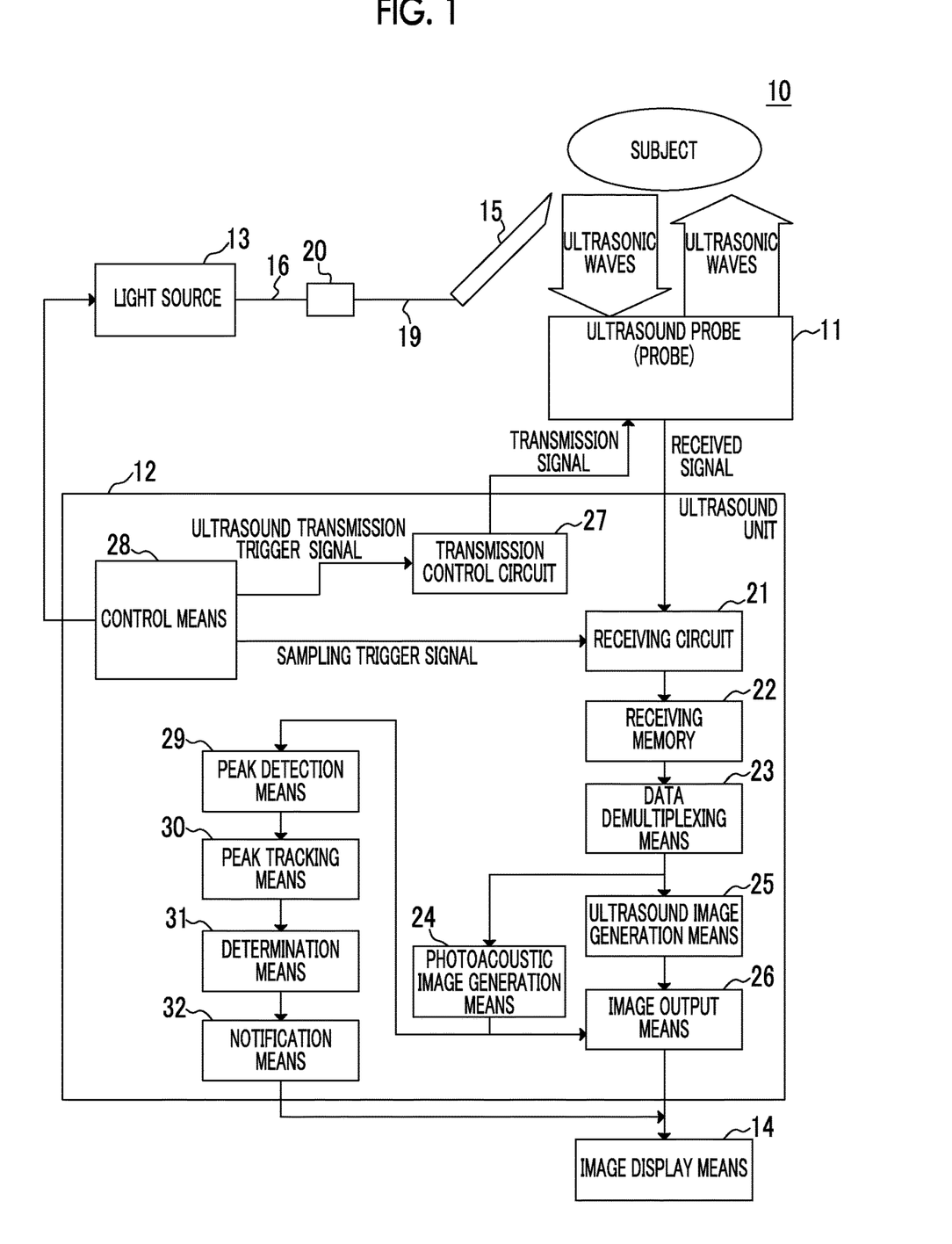
FIG. 1 is a block diagram illustrating a photoacoustic image generation apparatus according to a first embodiment of the invention.

Hereinafter, embodiments of the invention will be described in detail with reference to the drawings. FIG. 1 illustrates a photoacoustic image generation apparatus according to a first embodiment of the invention. A photoacoustic image generation apparatus 10 includes a probe (ultrasound probe) 11, an ultrasound unit 12, a light source (laser unit) 13, and a puncture needle 15. In the embodiment of the invention, ultrasonic waves are used as acoustic waves. However, the invention is not limited to the ultrasonic waves. Acoustic waves with an audible frequency may be used as long as an appropriate frequency can be selected according to, for example, an inspection target or measurement conditions.

The light source 13 emits light with a first wavelength. For example, the light source 13 emits pulsed light with a pulse energy of about 0.3 μJ to 30 μJ and a pulse time width of about 1 ns to 100 ns. The light source 13 is, for example, a solid-state laser light source. The type of light source is not particularly limited. The light source 13 may be a laser diode light source (semiconductor laser light source) or a light amplifying laser light source having a laser diode light source as a seed light source. In addition, light sources other than the laser light source may be used.

The puncture needle 15 is a needle that is inserted into a subject. An optical fiber 19 is inserted into the puncture needle 15. The optical fiber 19 is connected to light guide means, such as an optical fiber 16 on which light emitted from the light source 13 is incident, through an optical connector 20. The optical connector 20 detachably connects the optical fiber 16 and the optical fiber 19. The connection of the optical connector 20 is released to throw away the optical fiber 19 together with the puncture needle 15 at the same time.

Figure 2:
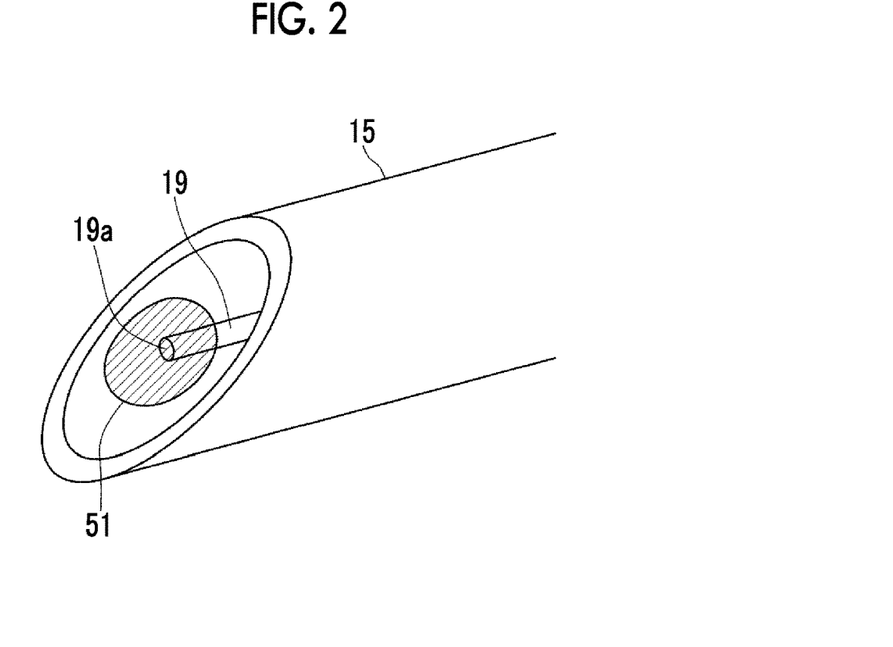
FIG. 2 is a perspective view illustrating the vicinity of a leading end of a puncture needle.

FIG. 2 illustrates the vicinity of a leading end of the puncture needle 15. The leading end (a far end as viewed from the light source side) of the optical fiber 19 forms a light emitting portion 19a from which guided light is emitted. The light emitting portion 19a is provided in the vicinity of the leading end of the puncture needle 15. The optical fiber 19 guides the light with the first wavelength which is incident from the light source side to the vicinity of the leading end of the puncture needle 15. The optical fiber 19 may be coated. For example, polyimide, a fluorine resin, or an acrylic resin may be used for coating.

The puncture needle 15 includes a light absorption/conversion member 51 provided in the vicinity of the leading end. The light absorption/conversion member 51 converts the light with the first wavelength emitted from the light emitting portion 19a into light with a second wavelength. The second wavelength is different from the first wavelength. In addition, the light absorption/conversion member 51 generates photoacoustic waves with the conversion into the light with the second wavelength. Hereinafter, the photoacoustic waves are referred to as first photoacoustic waves. The light absorption/conversion member 51 is provided in the vicinity of the leading end of the puncture needle 15 and can generate the first photoacoustic waves at a point in the vicinity of the leading end of the puncture needle 15. The length of a first photoacoustic wave generation source (sound source) is sufficiently less than the overall length of the puncture needle. Therefore, the sound source can be regarded as a point sound source.

Here, "the vicinity of the leading end" means a position where the light absorption/conversion member 51 provided at the leading end can generate photoacoustic waves capable of imaging the position of the leading end of the puncture needle 15 with accuracy required for a needling operation in a case in which the light emitting portion 19a is disposed at the position. For example, the vicinity of the leading end is the range of 0 mm to 3 mm from the leading end to the base end of the puncture needle 15.

The light absorption/conversion member 51 includes, for example, a phosphor that emits light with the second wavelength, using the light with the first wavelength as excitation light, and a resin, such as an epoxy resin including the phosphor. It is preferable that the phosphor emits light, for example, in a nanosecond order. For example, a quantum dot or an organic phosphor (organic pigment) is used as the phosphor. It is preferable that the quantum dot is a PbS-based quantum dot. For example, a quantum dot manufactured by Evident Technologies Inc. is used.

The light absorption/conversion member 51 may cover at least a part of the light emitting portion 19a. In addition, the light absorption/conversion member 51 may also function as a fixing member that fixes the optical fiber 19 to an inner wall of an inner cavity of the puncture needle 15.

The light with the second wavelength converted by the light absorption/conversion member 51 is emitted to the outside of the puncture needle 15. In a case in which an absorber that absorbs the light with the second wavelength is present in the emission range of the light with the second wavelength, the absorber generates photoacoustic waves. Hereinafter, the photoacoustic waves are referred to as second photoacoustic waves. For example, the second wavelength indicates absorptivity in the light absorbance-wavelength characteristics of a material (evaluation target material) that is present at a needling target position of the puncture needle 15.

The phosphor included in the light absorption/conversion member 51 is selected according to the material that is present in the vicinity of the part into which the puncture needle 15 is inserted. In other words, the phosphor is selected according to an evaluation target material in the surrounding environment of the puncture needle 15. For example, in a case in which the evaluation target material is a nerve, a phosphor that converts the light with the first wavelength (excitation light) into light with a wavelength of 1210 nm is selected as the phosphor included in the light absorption/conversion member 51. For example, a PbS-based phosphor is used as the phosphor.

In a case in which the evaluation target material is a contrast agent used to visualize, for example, a lymph node or a lymph tube, a phosphor that converts the light with the first wavelength into light with a wavelength (second wavelength) which is absorbed by the contrast agent to generate photoacoustic waves (second photoacoustic waves) may be used as the phosphor included in the light absorption/conversion member 51. For example, in a case in which indocyanine green (ICG) is used as the contrast agent, a phosphor that converts the excitation light into light with a wavelength of 800 nm may be used. Examples of the phosphor include PbS and CdTe. In a case in which methylene blue and Patent Blue V are used as the contrast agent, the absorption peaks of methylene blue and Patent Blue V are 663 nm and 638 nm, respectively. Therefore, in this case, a phosphor that converts the excitation light into light with a wavelength of 650 nm may be used. An example of the phosphor is InP/ZnS.

In a case in which a specific material is transferred to, for example, a cancer cell by a drug delivery system (DDS) and the material is evaluated as the evaluation target material, a phosphor that converts the light with the first wavelength into light with a wavelength (second wavelength) which is absorbed by the material to generate photoacoustic waves (second photoacoustic waves) may be used as the phosphor included in the light absorption/conversion member 51. For example, in a case in which the evaluation target is a gold nanoparticle, a phosphor that converts the excitation light into light with a wavelength selected from the wavelength range of 600 nm to 900 nm according to the diameter of the gold nanoparticle may be used. For example, there is CdTe as the phosphor that emits light with a wavelength of 770 nm.

Figure 3:
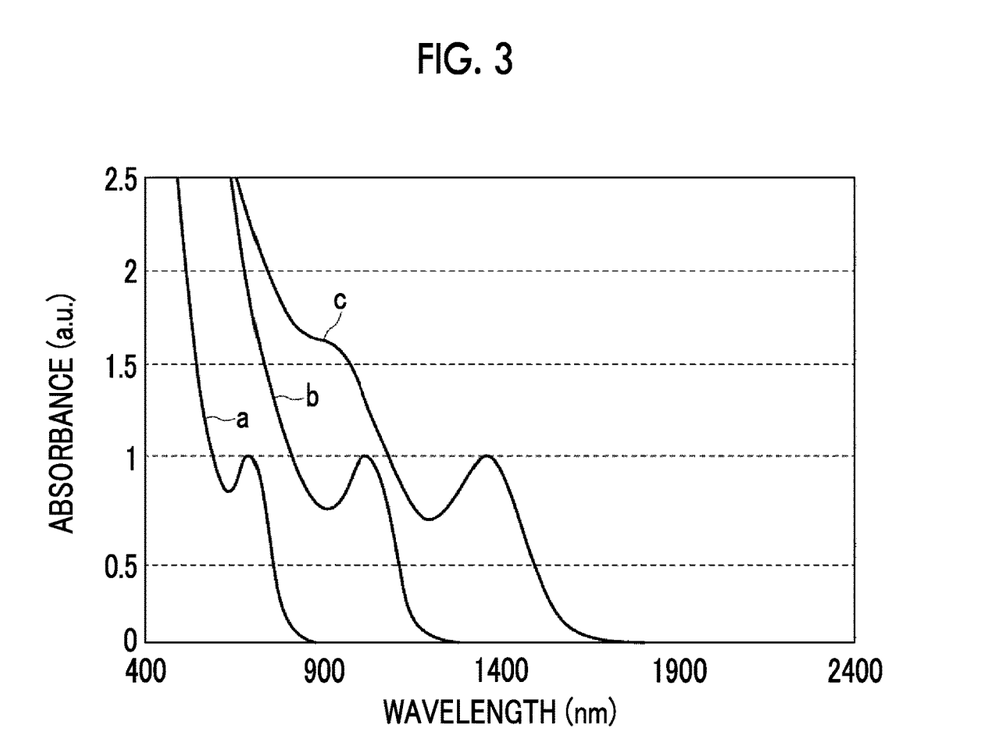
FIG. 3 is a graph illustrating the absorbance-wavelength characteristics of a phosphor.

FIG. 3 illustrates the absorbance-wavelength characteristics of the phosphor. The horizontal axis indicates a wavelength and the vertical axis indicates absorbance. FIG. 3 illustrates the absorbance-wavelength characteristics of three PbS-based phosphors (quantum dots) represented by graphs a to c. As can be seen from FIG. 3, these phosphors have high absorbance in the wavelength range of about 400 nm to 500 nm. Therefore, it is preferable that a light source which emits light with a wavelength of 400 nm to 500 nm is used as the light source 13.

Figure 4:
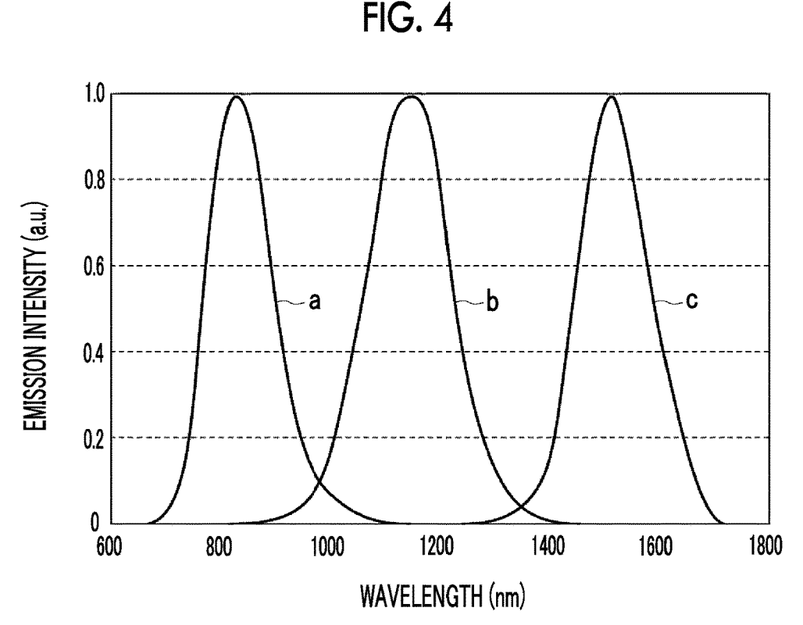
FIG. 4 is a graph illustrating the emission intensity-wavelength characteristics of the phosphor.

FIG. 4 illustrates the fluorescent emission intensity-wavelength characteristics of the phosphor. The horizontal axis indicates a wavelength and the vertical axis indicates emission intensity. FIG. 4 illustrates the emission intensity-wavelength characteristics of three PbS-based phosphors (quantum dots) represented by graphs a to c. The phosphor represented by the graph a converts the excitation light into fluorescent light with a wavelength of about 800 nm. The phosphor represented by the graph b converts the excitation light into fluorescent light with a wavelength of about 1100 nm. The phosphor represented by the graph c converts the excitation light into fluorescent light with a wavelength of about 1500 nm. It is possible to easily adjust the wavelength of the fluorescent light from the phosphors by changing the diameter of a fluorescent particle. An appropriate particle diameter is selected according to the purpose of use and is used in the light absorption/conversion member 51, which makes it possible to appropriately select the wavelength of light emitted to the subject while maintaining the wavelength of light from the light source 13. For example, the diameter of the fluorescent particle used in the graph a is 2.2 nm, the diameter of the fluorescent particle used in the graph b is 3.2 nm, and the diameter of the fluorescent particle used in the graph c is 5.3 nm. The phosphor may be a phosphor that can emit pulsed light in a nanosecond order. In addition, phosphors other than the quantum dot may be used. For example, a phosphor that uses an organic fluorescent pigment and has a high response speed may be used.

Figure 5:
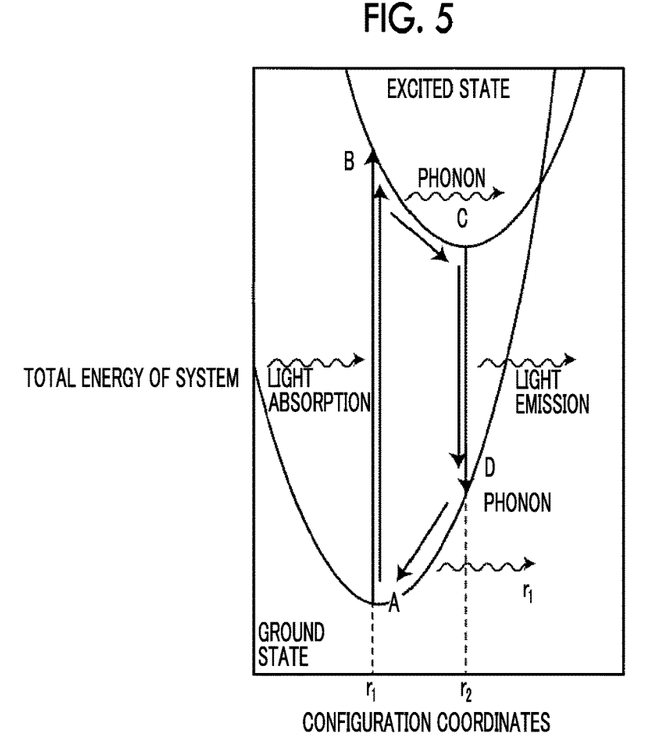
FIG. 5 is a diagram illustrating a configuration coordinate curve.

Here, a general mechanism in which the first photoacoustic waves are generated in the light absorption/conversion member 51 will be described. FIG. 5 illustrates a configuration coordinate curve. The form of a wave function is different in an excited state and a ground state and potentials received from peripheral atoms are different from each other. Therefore, as illustrated in FIG. 5, the configuration coordinates $r_2$ of an atom at which energy is the minimum in the excited state deviate from the configuration coordinates $r_1$ at which energy is the minimum in the ground state.

In a case in which light is incident on the phosphor and the phosphor absorbs light and moves to an excited state, the transition of an electron state occurs in a short time in proportion to the movement of an atomic nucleus and vertical transition from A to B in FIG. 5 occurs. B indicates an unstable excited state. In the excited state, thermal relaxation (lattice relaxation) occurs. That is, the phosphor emits heat and moves to C. The relaxation time is in the range of $10^{-12}$ s to $10^{-10}$ s (1 to 100 picoseconds).

Light emission from the excited state to the ground state occurs in the vertical direction from C to D. Since D is an unstable state, the phosphor emits phonons (heat) again and returns to A. The phosphor includes a thermal relaxation process from B to C and from D to A. Therefore, in a case in which pulsed light is emitted in a nanosecond order, the phosphor generates photoacoustic waves (first photoacoustic waves), in addition to emitting fluorescent light. In particular, in the case of a quantum dot phosphor, the energy level is further affected by the impurity level or the particle size of a doping element and an emission wavelength changes.

Figure 6:
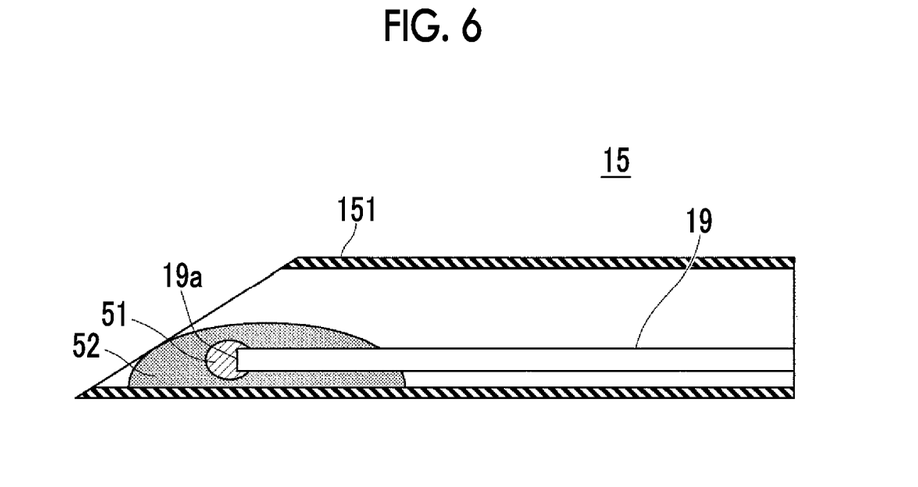
FIG. 6 is a cross-sectional view illustrating the vicinity of a leading end of a puncture needle according to a modification example.

The puncture needle 15 may include a transparent resin that transmits the light with the second wavelength. The light absorption/conversion member 51 (see FIG. 2) may be covered with the transparent resin. FIG. 6 is a cross-sectional view illustrating a leading end portion of the puncture needle 15 including the transparent resin. In the puncture needle 15, the light absorption/conversion member 51 is covered with a transparent resin 52. The transparent resin 52 transmits the light with the second wavelength. The transparent resin 52 may transmit most of incident light with the second wavelength and does not need to transmit all of the incident light with the second wavelength. That is, the transparent resin 52 does not need to transmit 100% of the light with the second wavelength. For example, a thermosetting epoxy resin (adhesive) or an ultraviolet-curable resin is used as the transparent resin 52.

A puncture needle main body 151 forming a main body portion of the puncture needle 15 has an inner cavity. The transparent resin 52 may also function as a fixing member that fixes the light absorption/conversion member 51 and the optical fiber 19 to the inner wall of the inner cavity of the puncture needle main body 151. In FIG. 6, the light absorption/conversion member 51 covers the light emitting portion 19a of the optical fiber 19 and (the leading end portion of) the optical fiber 19 and the light absorption/conversion member 51 are fixed to the inner wall of the puncture needle main body 151 by the transparent resin 52.

In general, the compatibility of a wavelength conversion material, such as a phosphor, with a living body is not guaranteed. Since the light absorption/conversion member 51 including a wavelength conversion material is covered with the transparent resin 52 having compatibility with a living body, it is possible to prevent the inflow of the light absorption/conversion member 51 or a portion thereof (particularly, the wavelength conversion material) into the living body.

Returning to FIG. 1, the probe 11 includes, for example, a plurality of detector elements (ultrasound oscillators) which are acoustic wave detection means and are one-dimensionally arranged. After the puncture needle 15 is inserted into the subject, the probe 11 detects the photoacoustic waves (first photoacoustic waves) generated from the light absorption/conversion member 51 (see FIG. 2) and the photoacoustic waves (second photoacoustic waves) generated by the absorption of the light with the second wavelength emitted from the light absorption/conversion member 51 by a light absorber. The probe 11 performs the transmission of acoustic waves (ultrasonic waves) to the subject and the reception of the reflected acoustic waves (reflected ultrasonic waves) with respect to the transmitted ultrasonic waves, in addition to the detection of the photoacoustic waves. The transmission and reception of the sound waves may be performed at different positions. For example, ultrasonic waves may be transmitted from a position different from the position of the probe 11 and the probe 11 may receive the reflected ultrasonic waves with respect to the transmitted ultrasonic waves. The probe 11 is not limited to a linear probe and may be a convex probe or a sector probe.

The ultrasound unit 12 includes a receiving circuit 21, a receiving memory 22, data demultiplexing means 23, photoacoustic image generation means 24, ultrasound image generation means 25, image output means 26, a transmission control circuit 27, control means 28, peak detection means 29, peak tracking means 30, determination means 31, and notification means 32. The ultrasound unit 12 forms a signal processing device. The ultrasound unit 12 typically includes a processor, a memory, and a bus. A program related to the generation of a photoacoustic image is incorporated into the ultrasound unit 12. The program is executed to implement the functions of at least some of the components in the ultrasound unit 12.

The receiving circuit 21 receives a detection signal output from the probe 11 and stores the received detection signal in the receiving memory 22. The receiving circuit 21 typically includes a low noise amplifier, a variable gain amplifier, a low-pass filter, and an analog-to-digital convertor (AD convertor). The detection signal from the probe 11 is amplified by the low noise amplifier. The gain of the detection signal is adjusted by the variable gain amplifier according to a depth and a high-frequency component of the detection signal is cut by the low-pass filter. Then, the detection signal is converted into a digital signal in the AD convertor and is stored in the receiving memory 22. The receiving circuit 21 includes, for example, one integral circuit (IC).

The probe 11 outputs a detection signal of the photoacoustic waves and a detection signal of the reflected ultrasonic waves. The AD-converted detection signals (sampling data) of the photoacoustic waves and the reflected ultrasonic waves are stored in the receiving memory 22. The data demultiplexing means 23 reads the sampling data of the detection signal of the photoacoustic waves from the receiving memory 22 and transmits the sampling data to the photoacoustic image generation means 24. In addition, the data demultiplexing means 23 reads the sampling data of the reflected ultrasonic waves from the receiving memory 22 and transmits the sampling data to the ultrasound image generation means (reflected acoustic image generation means) 25.

The photoacoustic image generation means 24 generates a photoacoustic image on the basis of the detection signal of the photoacoustic waves detected by the probe 11. The generation of the photoacoustic image includes, for example, image reconfiguration, such as phasing addition, detection, and logarithmic conversion. The ultrasound image generation means 25 generates an ultrasound image (reflected acoustic image) on the basis of the detection signal of the reflected ultrasonic waves detected by the probe 11. The generation of the ultrasound image includes, for example, image reconfiguration, such as phasing addition, detection, and logarithmic conversion. The image output means 26 outputs the photoacoustic image and the ultrasound image to image display means 14 such as a display device. The image output means 26 may also function as image combination means for combining the photoacoustic image with the ultrasound image and outputting a composite image to the image display means 14.

The control means 28 controls each component in the ultrasound unit 12. For example, in a case in which a photoacoustic image is acquired, the control means 28 transmits a trigger signal to the light source 13 such that the light source 13 emits laser light. In addition, the control means 28 transmits a sampling trigger signal to the receiving circuit 21 to control, for example, the sampling start time of the photoacoustic waves with the emission of the laser light.

In a case in which an ultrasound image is acquired, the control means 28 transmits an ultrasound transmission trigger signal for instructing the transmission of ultrasonic waves to the transmission control circuit 27. In a case in which the ultrasound transmission trigger signal is received, the transmission control circuit 27 directs the probe 11 to transmit ultrasonic waves. For example, the probe 11 performs scanning while shifting acoustic lines one by one to detect reflected ultrasonic waves. The control means 28 transmits a sampling trigger signal to the receiving circuit 21 in synchronization with the transmission of the ultrasonic waves to start the sampling of the reflected ultrasonic waves.

Here, in this embodiment, the probe 11 detects the first photoacoustic waves generated from the light absorption/conversion member 51 and the second photoacoustic waves generated by the absorption of the light with the second wavelength converted by the light absorption/conversion member 51 by the subject. In general, the photoacoustic wave generation source appears as a bright point in the photoacoustic image. A bright point corresponding to the generation source of the first photoacoustic waves indicates the positional information of the puncture needle. In contrast, a bright point corresponding to the generation source of the second photoacoustic waves appears in a case in which a specific material that absorbs the light with the second wavelength is present in the vicinity of the puncture needle 15. The bright point indicates the surrounding environment information of the puncture needle 15.

In this embodiment, since there are two generation sources of the photoacoustic waves which are created as images in the photoacoustic image, two bright points are mixed in the photoacoustic image. In some cases, since the intensity of the detected photoacoustic waves is sequentially changed by the movement of the body or the movement of the probe, a bright point blinks in the photoacoustic image. The observation of the photoacoustic image makes it possible to check the position of the puncture needle 15 and to evaluate the surrounding environment. However, since two bright points blink independently, it is considered that only the display of an image is insufficient to distinguish the point indicating the positional information of the puncture needle from the point indicating the surrounding environment information in the photoacoustic image.

For this reason, in this embodiment, the positional information and the surrounding environment information of the puncture needle 15 are separated from each other. The peak detection means 29 detects one or more peaks having a higher signal value (signal intensity) than the surroundings in the photoacoustic image. For example, the peak detection means 29 detects the peak, a portion having a signal value that is equal to or greater than a threshold value in the surroundings. In particular, in an early stage of the insertion of the puncture needle 15, one peak is detected. It is considered that the peak corresponds to the generation source of the first photoacoustic waves. That is, It is considered that the peak indicates the position of the tip of the needle. The position of the peak is detected to detect the tip of the needle. In a case in which the leading end of the puncture needle 15 is close to a material (evaluation target material) that absorbs the light with the second wavelength, two peaks are detected. One of the two peaks indicates the position of the leading end of the puncture needle and the other peak indicates the presence of an evaluation target material. In a case in which the leading end of the puncture needle 15 and the evaluation target material are so close that they cannot be separated, one peak is detected.

Figure 7:
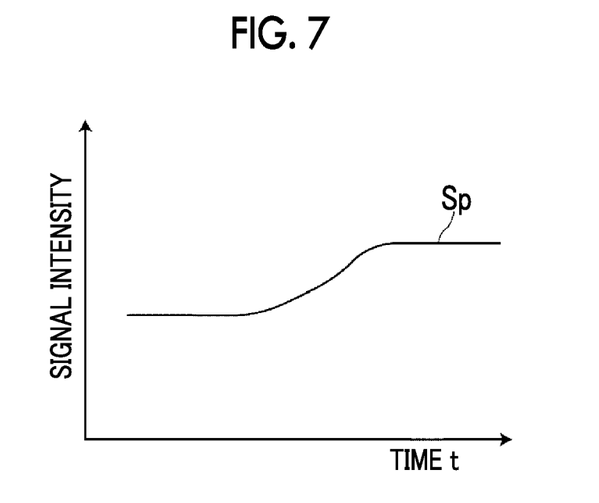
FIG. 7 is a graph illustrating a change in a signal value of a peak over time.

The peak tracking means 30 temporally tracks the signal value of the detected peak. FIG. 7 illustrates a change in the signal value of the peak over time. The horizontal axis indicates time and the vertical axis indicates the magnitude of the signal value (signal intensity). In an early stage of needling, only the first photoacoustic waves are substantially detected. The first photoacoustic waves are generated with constant intensity. Therefore, there is little change in the signal value SP of the peak. As the leading end of the puncture needle 15 becomes closer to the evaluation target material, the signal value of a region corresponding to the leading end portion of the puncture needle 15 in the photoacoustic image becomes larger and the signal value SP of the peak becomes larger. In a case in which the leading end of the puncture needle 15 and the evaluation target material are so close that they cannot be separated, the signal value SP of the peak is the maximum and tends to be saturated.

The determination means 31 determines whether the leading end of the puncture needle 15 is closed to the material (evaluation target material) that absorbs the light with the second wavelength and generates the second photoacoustic waves, on the basis of a change in the signal value of the tracked peak. For example, in a case in which the change in the signal value of the peak is equal to or greater than a threshold value, the determination means 31 determines that the leading end of the puncture needle 15 is close to the evaluation target material. For example, as an example of the change in the signal value of the peak, the determination means 31 stores the signal value of the peak in the early stage of needling and calculates the difference between the signal value and a signal value of the current peak. The determination means 31 determines the closeness between the puncture needle 15 and the evaluation target material on the basis of the calculated difference. For example, the determination means 31 may determine that the puncture needle 15 is close to the evaluation target material in a case in which the signal value of the current peak is greater than the signal value of the peak in the early stage by the threshold value or more.

As another example of the change in the signal value of the peak, the determination means 31 may determine a change in the signal value of the peak on the basis of the temporal differentiation of the signal value of the temporally tracked peak, instead of using the difference. For example, the determination means 31 may determine that the puncture needle 15 is close to the evaluation target material in a case in which there is a rapid change in the temporal differentiation of the signal value of the peak, for example, in a case in which positive and negative values are reversed or a differential value increases significantly. In addition to the above, the determination means 31 may determine whether the puncture needle 15 is close to the evaluation target material in a case in which the peak tracking means has detected two peaks.

The notification means 32 notifies the determination result of the determination means 31. In a case in which the determination means 31 determines that the puncture needle 15 is close to the evaluation target material, the notification means 32 displays the determination result on the image display means 14. The notification means 32 may display the degree of change in the signal value of the tracked peak on the image display means 14. For example, the notification means 32 displays the magnitude of a change in the signal value of the peak. The user can determine that the puncture needle 15 is close to the evaluation target material to some extent, with reference to the indicator.

In addition, the signal intensity of the photoacoustic image varies depending on, for example, the attenuation of the acoustic waves in the depth direction or a difference in the number of receiving openings in the positional relationship with an oscillator array, according to the position of the leading end of the puncture needle 15 in an image. An intensity distribution in a case in which there is no material absorbing the second wavelength may be stored as background data and the background data may be compared with the current signal intensity to improve the accuracy of determination.

Figure 8:
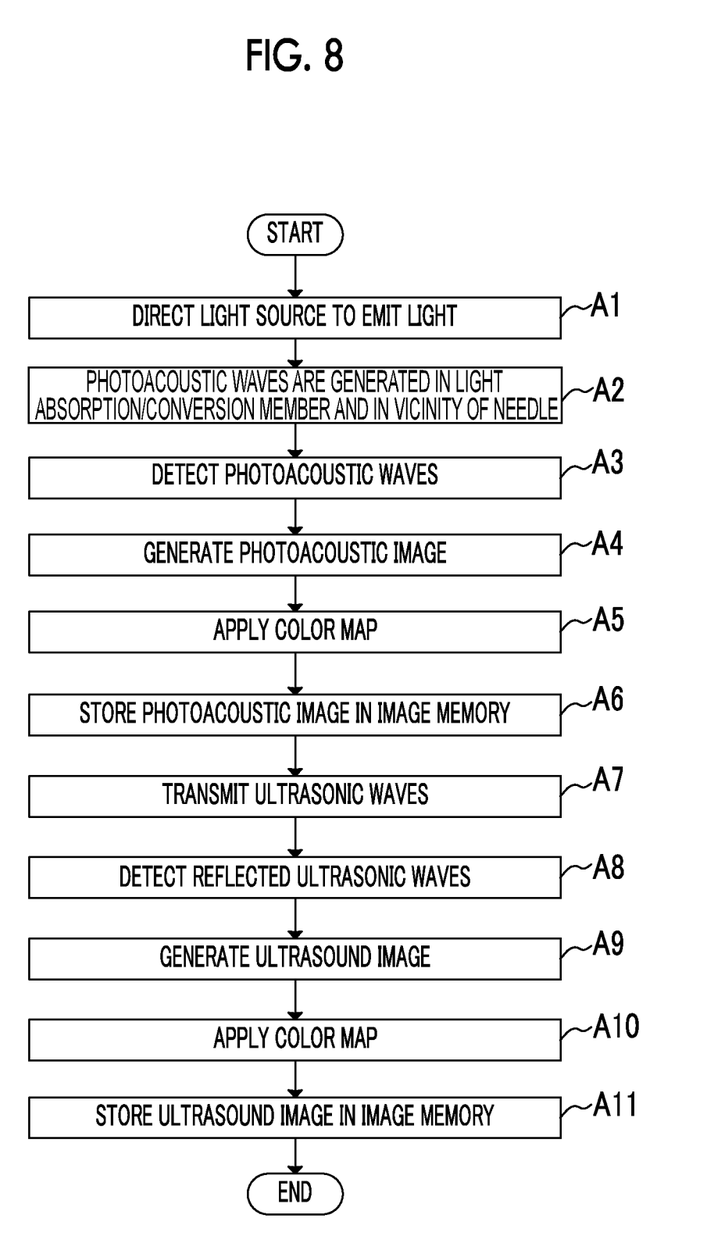
FIG. 8 is a flowchart illustrating the procedure of an image generation operation of the photoacoustic image generation apparatus.

Next, the procedure of an operation will be described. FIG. 8 illustrates the procedure of an image generation operation of the photoacoustic image generation apparatus 10. The control means 28 directs the light source 13 to emit light (Step A1). In Step A1, the control means 28 transmits a trigger signal to the light source 13. In a case in which the light source 13 is a solid-state laser device including a flash lamp and a Q-switch, the trigger signal includes, for example, a flash lamp trigger signal and a Q-switch trigger signal. In the light source 13, the flash lamp is turned on in response to the flash lamp trigger signal and then the Q-switch is driven in response to the Q-switch trigger signal to emit pulsed laser light with the first wavelength. In a case in which the light source 13 is a laser diode, a laser driver circuit makes a predetermined amount of current flow to the laser diode for the time corresponding to a pulse width in response to the trigger signal to emit pulsed laser light with the first wavelength.

The pulsed laser light emitted from the light source 13 is incident on the optical fiber 19 through the optical fiber 16 and the optical connector 20, is guided to the vicinity of the leading end of the puncture needle 15 by the optical fiber 19, and is emitted from the light emitting portion 19a (see FIG. 2). The light emitted from the light emitting portion 19a is converted into light with the second wavelength by the light absorption/conversion member 51. The light absorption/conversion member 51 generates the first photoacoustic waves during the process of converting the light into the light with the second wavelength (Step A2). In a case in which an absorber that absorbs the light with the second wavelength is present in the emission range of the light with the second wavelength converted by the light absorption/conversion member 51, the second photoacoustic waves are generated from the absorber.

The probe 11 detects the photoacoustic waves generated by the emission of the laser light, that is, the first photoacoustic waves generated from the light absorption/conversion member 51 and the second photoacoustic waves generated from the light absorber present in the vicinity of the puncture needle 15 (Step A3). The photoacoustic waves detected by the probe are received by the receiving circuit 21 and the sampling data of the photoacoustic waves is stored in the receiving memory 22. The photoacoustic image generation means 24 receives the sampling data of the detection signal of the photoacoustic waves through the data demultiplexing means 23 and generates a photoacoustic image (Step A4). The photoacoustic image generation means 24 may apply a color map (Step A5) to convert the signal intensity of the photoacoustic image into a color. The photoacoustic image generated by the photoacoustic image generation means 24 is stored in, for example, an image memory (not illustrated) of the image output means 26 (Step A6).

The control means 28 transmits an ultrasound trigger signal to the transmission control circuit 27. The transmission control circuit 27 directs the probe 11 to transmit ultrasonic waves in response to the ultrasound trigger signal (Step A7). The probe 11 transmits ultrasonic waves and detects reflected ultrasonic waves (Step A8). The reflected ultrasonic waves detected by the probe 11 are received by the receiving circuit 21 and the sampling data of the reflected ultrasonic waves is stored in the receiving memory 22. The ultrasound image generation means 25 receives the sampling data of the detection signal of the reflected ultrasonic waves through the data demultiplexing means 23 and generates an ultrasound image (Step A9). The ultrasound image generation means 25 may apply a color map (Step A10) to convert the signal intensity of the ultrasound image into a color. The ultrasound image generated by the ultrasound image generation means 25 is stored in, for example, the image memory (not illustrated) of the image output means 26 (Step A11).

Steps A1 to A11 are repeatedly performed to generate a plurality of photoacoustic images and ultrasound images in time series. The generation of the photoacoustic image and the generation of the ultrasound image may be performed in any order. Alternatively, the transmission of the ultrasonic waves, the detection of the reflected ultrasonic waves, and the generation of the ultrasound image may be omitted. The generation of one ultrasound image may include a process of transmitting the ultrasonic waves a plurality of times and the detection of the reflected ultrasonic waves. In addition, the generation of one photoacoustic image may include a process of emitting light a plurality of times and the detection of the photoacoustic waves. In these cases, the emission of light and the detection of the photoacoustic waves may be performed between the transmission of the ultrasonic waves and the detection of the reflected ultrasonic waves.

Figure 9:
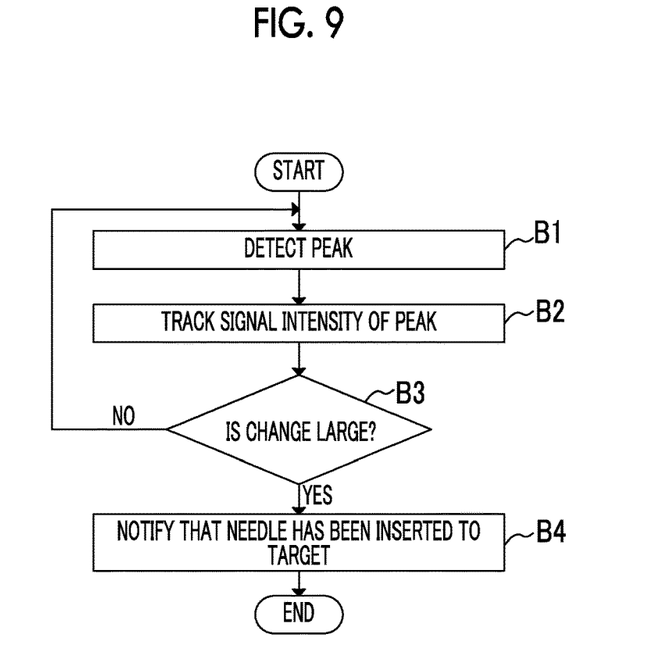
FIG. 9 is a flowchart illustrating the procedure of determining whether the leading end of the puncture needle is close to an evaluation target material.

FIG. 9 illustrates the procedure of a process of determining whether the leading end of the puncture needle 15 is close to the evaluation target material. The peak detection means 29 detects a peak with a higher signal value (signal intensity) than the surroundings in the photoacoustic image (Step B1). The peak detection means 29 detects the peak in each of the plurality of photoacoustic images generated in time series. The peak tracking means 30 temporally tracks the signal value of the detected peak (Step B2).

The determination means 31 determines whether a change in the signal value of the tracked peak is equal to or greater than the threshold value (Step B3). For example, the determination means 31 determines whether the difference between the signal value of the peak in the photoacoustic image generated in an early stage of needling and the signal value of the peak in the latest photoacoustic image is equal to or greater than the threshold value. The photoacoustic image generated in the early stage of needling can be a photoacoustic image in which a bright point appears due to the first photoacoustic waves. In a case in which the change in the signal value of the peak is less than the threshold value, the process returns to Step B1.

In a case in which it is determined in Step B3 that the difference is equal to or greater than the threshold value, the notification means 32 notifies the user that the leading end of the puncture needle 15 is close to the evaluation target material (Step B4). For example, the notification means 32 displays a message indicating that the puncture needle 15 has been inserted into the target on the image display means 14 in Step B4.

In this embodiment, the puncture needle 15 includes the light absorption/conversion member 51 that converts the light with the first wavelength into the light with the second wavelength. The light absorption/conversion member 51 generates the first photoacoustic waves during the conversion. In addition, the light with the second wavelength converted by the light absorption/conversion member 51 is emitted from the leading end of the puncture needle 15 to the subject. In a case in which the light absorber that absorbs the light with the second wavelength is present in the part irradiated with the light with the second wavelength in the subject, the second photoacoustic waves are generated from the light absorber. The first photoacoustic waves and the second photoacoustic waves are detected and a photoacoustic image is generated on the basis of the detected photoacoustic waves. In this way, the positional information and the surrounding environment information of the leading end of the puncture needle 15 can be included in the photoacoustic image. For example, the user, such as a doctor, can observe the photoacoustic image, recognize that the number of bright points has increased from 1 to 2, and determine that the leading end of the puncture needle 15 has been inserted to the part in which the evaluation target material is present.

In this embodiment, the phosphor used is changed to change the wavelength of fluorescent light. For example, a plurality of puncture needles 15 are prepared and different phosphors are included in the light absorption/conversion members 51 of the puncture needles 15. In this case, the wavelength (second wavelength) of light to be converted is appropriately selected according to the evaluation target material. According to this structure, it is possible to change the wavelength of light emitted to the subject only by changing the puncture needle 15 to be used, without changing the wavelength of light emitted from the light source 13. Therefore, even in a case in which a plurality of light sources that emit light components with a plurality of wavelengths are not prepared, it is possible to evaluate whether a plurality of materials with different absorption wavelengths are present in the vicinity of the puncture needle and thus to reduce the overall cost of the apparatus.

In this embodiment, the peak detection means 29 detects a peak from a photoacoustic image and the peak tracking means 30 temporally tracks the signal value of the detected peak. The determination means 31 determines whether the puncture needle 15 is close to the evaluation target material on the basis of a change in the signal value of the peak. In a case in which the distance between the leading end of the puncture needle 15 and the evaluation target material is long, the light with the second wavelength generated from the light absorption/conversion member 51 does not reach the evaluation target material and only the first photoacoustic waves are generated. In a case in which the leading end of the puncture needle 15 is close to the evaluation target material, the evaluation target material is irradiated with the light with the second wavelength and the second photoacoustic waves are generated in addition to the first photoacoustic waves. It is considered that the signal value of the peak in the photoacoustic image is increased by the generation of the second photoacoustic waves. In this embodiment, both the positional information and the surrounding environment information of the leading end of the puncture needle 15 are included in the photoacoustic image. Therefore, in some cases, only the observation of the photoacoustic image is insufficient to distinguish the part indicating the positional information from the part indicating the surrounding environment information. For this reason, the signal value of the peak is temporally tracked and a change in the signal value over time is observed, which makes it possible to determine whether the leading end of the puncture needle 15 is close to the evaluation target material even in a case in which it is difficult to distinguish the information items.

Figure 10:
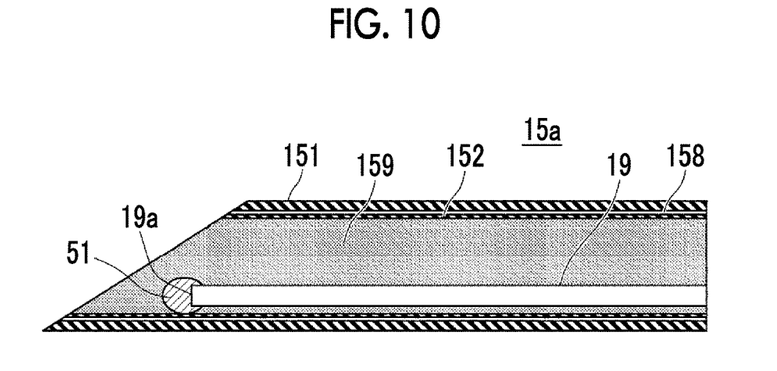
FIG. 10 is a cross-sectional view illustrating the vicinity of a leading end of a puncture needle according to a second embodiment of the invention.

Next, a second embodiment of the invention will be described. This embodiment differs from the first embodiment in that the puncture needle 15 includes an outer needle and an inner needle. The other configurations may be the same as those in the first embodiment.

FIG. 10 is a cross-sectional view illustrating a puncture needle 15a according to this embodiment. A puncture needle main body 151 forming the outer needle has an opening at an acute leading end and has an inner cavity. An inner needle 152 has substantially the same inside diameter as the inner cavity of the puncture needle main body 151 and is configured so as to be inserted into or removed from the hollow puncture needle main body 151. The inner needle 152 is inserted into the inner cavity of the puncture needle main body 151 from the base end side of the puncture needle main body 151 to seal at least a portion of the inner cavity of the puncture needle main body 151 to the extent that, for example, a section of the living body is prevented from being inserted into the inner cavity. A protruding portion for connection position adjustment is provided in a base end portion of the inner needle 152. A groove into which the protruding portion provided in the base end portion of the inner needle 152 is fitted is provided in a base end portion of the puncture needle main body 151. In a case in which the inner needle 152 is set in the puncture needle main body 151, the protruding portion provided in the base end portion of the inner needle 152 and the groove provided in the base end portion of the puncture needle main body 151 are positioned and the base end portion of the inner needle 152 is fitted to the base end portion of the puncture needle main body 151.

The inner needle 152 includes the optical fiber 19, the light absorption/conversion member 51, a tube 158, and a transparent resin 159. The tube 158 is, for example, a hollow tube made of polyimide. The tube 158 may be a metal tube made of, for example, stainless steel. The outside diameter of the tube 158 is slightly less than the diameter of the inner cavity of the puncture needle main body 151. The transparent resin 159 is provided in the tube 158. The transparent resin 159 transmits the light with the second wavelength. For example, an epoxy resin (adhesive) is used as the transparent resin 159. The tube 158 and the transparent resin 159 are acute, similarly to the acute leading end of the puncture needle. A photocurable resin, a thermosetting resin, or a room-temperature-curable resin may be used as the transparent resin 159.

The optical fiber 19 is covered with the transparent resin 159 in the tube 158. The light absorption/conversion member 51 is provided at the leading end of the optical fiber 19. The light absorption/conversion member 51 is irradiated with the light emitted from the light emitting portion 19a. In a case in which the light source 13 (see FIG. 1) emits light, the light absorption/conversion member 51 absorbs the emitted light with the first wavelength and photoacoustic waves are generated at the leading end of the puncture needle. In addition, the light with the second wavelength converted by the light absorption/conversion member 51 is emitted to the outside.

An operator, such as a doctor, inserts the puncture needle 15a into the subject, with the inner needle 152 set in the puncture needle main body 151. Since the inner cavity of the puncture needle main body 151 is closed by the inner needle 152, it is possible to prevent a piece of flesh from getting into the needle while the needle is being inserted and thus to prevent the needling sense of the operator from being hindered. In addition, it is possible to prevent the inflow of water from the part to be needled to the inner cavity of the puncture needle main body 151. After inserting the needle into the subject, the operator releases the connection between the base end portion of the inner needle 152 and the base end portion of the puncture needle main body 151 and takes the inner needle 152 out of the puncture needle main body 151. After taking the inner needle 152 out of the puncture needle main body 151, the operator can attach, for example, a syringe to the base end portion of the puncture needle main body 151 and inject a medicine such as an anesthetic.

Figure 11:
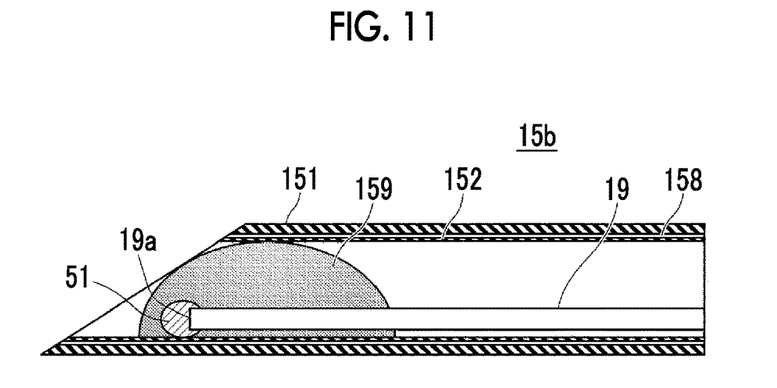
FIG. 11 is a cross-sectional view illustrating the vicinity of a leading end of a puncture needle according to a modification example.

In addition, the transparent resin 159 may close at least a leading end portion of the tube 158 and does not necessarily close the entire inside of the tube 158. FIG. 11 is a cross-sectional view illustrating the vicinity of the leading end of a puncture needle according to a modification example. In a puncture needle 15b, a transparent resin 159 covers the light absorption/conversion member 51 covering the light emitting portion 19a of the optical fiber 19 and (the leading end portion of) the optical fiber 19 and the light absorption/conversion member 51 are fixed to the inner wall of the tube 158 by the transparent resin 159. In addition, the transparent resin 159 closes an opening provided in the leading end portion of the tube 158. In a case in which this configuration is used, it is also possible to prevent the inflow of, for example, water into the inner needle 152. Furthermore, it is possible to obtain the effect of preventing the inflow of the light absorption/conversion member 51 or a portion thereof (particularly, a wavelength conversion material) into the living body.

The optical fiber 19 does not need to be fixed to the inner wall of the tube 158 by the transparent resin 159 and may be fixed to the inner wall of the tube 158 by the light absorption/conversion member 51. The leading end portion of the tube 158 may be closed by the light absorption/conversion member 51. In this case, the transparent resin 159 may be omitted. In addition, instead of covering the optical fiber 19 with the transparent resin 159, the optical fiber 19 may be covered with a resin with which the same phosphor as that included in the light absorption/conversion member 51 is mixed.

In this embodiment, the puncture needle 15a includes the inner needle 152 provided in the inner cavity of the puncture needle main body 151. The inner needle 152 closes the inner cavity of the puncture needle main body 151 while the puncture needle 15a is being inserted. Therefore, it is possible to prevent the needling sense of the operator from being hindered and to prevent the inflow of water from the part to be needled to the inner cavity of the puncture needle main body 151. The other effects are the same as those in the first embodiment.

In the above-described embodiments, the puncture needle 15 is considered as an insert. However, the invention is not limited thereto. The insert may be a radio frequency ablation needle including an electrode that is used for radio frequency ablation, a catheter that is inserted into a blood vessel, or a guide wire for a catheter that is inserted into a blood vessel. Alternatively, the insert may be an optical fiber for laser treatment.

In the above-described embodiments, a needle having an opening at the leading end is assumed as the needle. However, the opening is not necessarily provided at the leading end of the needle. The needle is not limited to an injection needle and may be a biopsy needle used for biopsy. That is, the needle may be a biopsy needle that is inserted into an inspection target of the living body and extracts the tissues of a biopsy site of the inspection target. In this case, photoacoustic waves may be generated from an extraction portion (intake port) for sucking and extracting the tissues of the biopsy site. In addition, the needle may be used as a guiding needle that is used for insertion to a deep part, such as a part under the skin or an organ inside the abdomen.

The puncture needle 15 is not limited to the needle that is inserted from the outside of the subject into the subject through the skin and may be a needle for ultrasound endoscopy. The optical fiber 19 and the light absorption/conversion member 51 may be provided in the needle for ultrasound endoscopy. The light absorption/conversion member 51 provided in the leading end portion of the needle may be irradiated with light with the first wavelength. Photoacoustic waves may be detected and a photoacoustic image may be generated. In this case, it is possible to perform needling while observing the photoacoustic image and checking the position of the leading end portion of the needle for ultrasound endoscopy. In addition, it is possible to determine whether an evaluation target material is present in the vicinity of the needle. The first photoacoustic waves generated from the leading end portion of the needle for ultrasound endoscopy and the second photoacoustic waves generated from the vicinity of the leading end portion may be detected by a probe for body surface or a probe that is incorporated into an endoscope.

In the second embodiment, the example in which the inner needle 152 (see FIG. 10) includes the tube 158 has been described. However, the invention is not limited thereto. Instead of the configuration in which the tube 158 is used and the optical fiber 19 is covered with the transparent resin 159 in the tube 158, the optical fiber 19 that has an outside diameter substantially equal to the inside diameter of the puncture needle main body 151 may be used as the inner needle. Alternatively, an optical fiber that is coated with polyimide or a resin, such as a fluoride resin or an acrylic resin, in advance may be used.

However, in JP2013-13713A, both the photoacoustic waves generated by the absorption of light emitted from the light emitting portion by the light absorber that is present in front of the needle in the needling direction in the subject and the photoacoustic waves generated by the absorption of the light emitted from the light emitting portion by, for example, metal forming the puncture needle main body are detected. In this case, since there are two generation sources of the photoacoustic waves, two bright points are mixed in the photoacoustic image. In the system disclosed in JP2013-13713A, the positional information and the surrounding environment information of the puncture needle 15 may be separated by the same process as that described in the first embodiment.

As another example of the puncture needle, a puncture needle is considered which includes a light absorption member that absorbs light with a certain wavelength (third wavelength) emitted from the light emitting portion 19a, generates photoacoustic waves, and transmits light with another wavelength (fourth wavelength) emitted from the light emitting portion 19a, instead of the light absorption/conversion member 51 (see FIG. 2). In a case in which this puncture needle is used, the photoacoustic image generation apparatus includes a light source that emits light with a third wavelength and a light source that emits light with a fourth wavelength. Light emitted from the light source that emits light with the third wavelength and light emitted from the light source that emits light with the fourth wavelength are multiplexed by, for example, a wavelength division multiplexing coupler and are incident on the optical fiber 19.

For example, in a case in which the third wavelength is 905 nm, the following material can be used as the light absorber included in the light absorption member: YKR-2900 or YKR-2081 which is a phthalocyanine-based material manufactured by Yamamoto Chemical Industry Co., Ltd.; FDN-004 or FDN-005 manufactured by Yamada Chemical Co., Ltd.; a cyanine-based absorber material disclosed in JP5243056B; IRA908, IRA912, or IRA931 manufactured by Exciton Inc.; or S0433 manufactured by FEW Chemicals GmbH. For example, the fourth wavelength may be appropriately selected from the range of 400 nm to 650 nm or the range of 1000 nm or more in which the light absorbance of the light absorber is low.

In the above-mentioned photoacoustic image generation apparatus, in a case in which two light sources emit light at the same time, light with the third wavelength is absorbed by the light absorption member and photoacoustic waves are generated. Light with the fourth wavelength is transmitted through the light absorption member and is emitted to the subject. In a case in which a material that absorbs the light with the fourth wavelength and generates photoacoustic waves is present in the emission range of the light with the fourth wavelength, photoacoustic waves are generated from the material. In this case, similarly to the case disclosed in JP2013-13713A, since there are two generation sources of photoacoustic waves, two bright points are mixed in the photoacoustic image. Therefore, in the photoacoustic image generation apparatus having the above-mentioned configuration, the positional information and the surrounding environment information of the puncture needle 15 may be separated by the same process as that described in the first embodiment.

The invention has been described above on the basis of the preferred embodiments. However, the photoacoustic image generation apparatus and the insert according to the invention are not limited to the above-described embodiments. Various modifications and changes of the configurations according to the above-described embodiments are also included in the scope of the invention.

EXPLANATION OF REFERENCES

10: photoacoustic image generation apparatus
11: probe
12: ultrasound unit
13: light source
14: image display means
15: puncture needle 16: optical fiber
19: optical fiber
19a: light emitting portion
20: optical connector
21: receiving circuit
22: receiving memory
23: data demultiplexing means
24: photoacoustic image generation means
25: ultrasound image generation means
26: image output means
27: transmission control circuit
28: control means
29: peak detection means
30: peak tracking means
31: determination means
32: notification means
51: light absorption/conversion member
52: transparent resin
151: puncture needle main body (outer needle)
152: inner needle
158: tube
159: transparent resin

What is claimed is:

1. An insert that is at least partially inserted into a subject, comprising:
   an optical fiber that guides light with a first wavelength received from light sources emitting light of more than one wavelength;
   a light emitting portion, formed by a leading end of the optical fiber, wherein the light emitting portion emits light guided by the optical fiber; and
   a light absorption/conversion member that absorbs the light with the first wavelength emitted from the light emitting portion, wherein the light absorption/conversion member comprises a phosphor of a material selected according to an evaluation target material, wherein the phosphor:
      absorbs the light with the first wavelength emitted from the light emitting portion,
      converts the light with the first wavelength into light with a second wavelength different from the first wavelength,
      based on the absorbing the light with the first wavelength emitted from the light emitting portion, generates photoacoustic waves with the conversion into the light with the second wavelength, and
      emits the photoacoustic waves and the light with the second wavelength, and wherein the second wavelength is constant and is controlled by the material of the phosphor.

2. The insert according to claim 1, wherein the light absorption/conversion member covers at least a part of a light emission surface of the light emitting portion.

3. The insert according to claim 1, wherein the insert has an inner cavity, and the light absorption/conversion member functions as a fixing member that fixes the optical fiber to an inner wall of the inner cavity.

4. The insert according to any one of claim 1, further comprising:
   a transparent resin that transmits the light with the second wavelength, wherein the light absorption/conversion member is covered with the transparent resin.

5. The insert according to claim 4, wherein the insert has an inner cavity, and the optical fiber and the light absorption/conversion member are fixed to an inner wall of the inner cavity by the transparent resin.

6. The insert according to claim 1, wherein the insert is a puncture needle having an inner cavity, and the insert further includes a hollow tube in which the optical fiber is accommodated.

7. The insert according to claim 6, wherein the puncture needle includes an inner needle and an outer needle, the inner needle includes the hollow tube, and the inner needle seals at least a portion of the inner cavity.

8. The insert according to claim 6, wherein the light absorption/conversion member functions as a fixing member that fixes the optical fiber to an inner wall of the hollow tube.

9. The insert according to claim 6, further comprising:
   a transparent resin that transmits the light with the second wavelength, wherein the optical fiber and the light absorption/conversion member are fixed to an inner wall of the hollow tube by the transparent resin.

10. A photoacoustic image generation apparatus comprising:
   light sources that emit light with a first wavelength, wherein the first wavelength is selected from a group of different wavelengths based on a light source of the light sources emitting the first wavelength;
   an insert that is at least partially inserted into a subject, the insert comprising:
      an optical fiber that guides the light with the first wavelength;
      a light emitting portion, formed by a leading end of the optical fiber, wherein the light emitting portion emits light guided by the optical fiber; and
      a light absorption/conversion member that absorbs the light with the first wavelength emitted from the light emitting portion, wherein the light absorption/conversion member comprises a phosphor of a material selected according to an evaluation target material, wherein the phosphor:
         absorbs the light with the first wavelength emitted from the light emitting portion,
         converts the light with the first wavelength into light with a second wavelength different from the first wavelength, and
         based on the absorbing the light with the first wavelength emitted from the light emitting portion generates first photoacoustic waves with the conversion into the light with the second wavelength, wherein the second wavelength is constant and is controlled by the material of the phosphor;
   an acoustic wave detection member, including a plurality of detector elements, that detects the first photoacoustic waves and second photoacoustic waves which are generated in the subject by the emission of the light with the second wavelength to the subject; and
   a processor configured to generate a photoacoustic image based on the first photoacoustic waves and the second photoacoustic waves.

11. The photoacoustic image generation apparatus according to claim 10, wherein the processor is further configured to detect one or more peaks having a larger signal value than the surroundings in the photoacoustic image.

12. The photoacoustic image generation apparatus according to claim 11, wherein the processor is further configured to:
   temporally track the signal value of the detected peak;
   determine whether the insert is close to a material that generates the photoacoustic waves, based on a change in the tracked signal value; and
   determine a determination result.

13. The photoacoustic image generation apparatus according to claim 12, wherein, in a case in which the processor detects two peaks, the processor is further configured to determine that the insert is close to the material that generates the second photoacoustic waves.

14. The photoacoustic image generation apparatus according to claim 12, wherein, in a case in which the change in the signal value is equal to or greater than a threshold value, the processor is further configured to determine that the insert is close to the material that generates the second photoacoustic waves.

15. The photoacoustic image generation apparatus according to claim 10, wherein the second wavelength is a wavelength indicating absorptivity in light absorbance-wavelength characteristics of a material that is present at an insertion target position of the insert.

16. The photoacoustic image generation apparatus according to claim 10, wherein the acoustic wave detection member further detects reflected acoustic waves with respect to acoustic waves transmitted to the subject, and the processor is further configured to generate a reflected acoustic image on the basis of the reflected acoustic waves.

\* \* \* \* \*